United States Patent [19]

Anderson

[11] 3,932,530

[45] Jan. 13, 1976

[54] PHENOXYPHENYL-BUTADIENOLS
[75] Inventor: Paul L. Anderson, Dover, N.J.
[73] Assignee: Sandoz, Inc., E. Hanover, N.J.
[22] Filed: Dec. 28, 1973
[21] Appl. No.: 429,402

[52] U.S. Cl............ 260/613 R; 424/340; 260/345.9; 260/347.8; 260/567.6 M; 260/456 R; 260/247.7; 260/293.9; 260/326.8; 260/501.15
[51] Int. Cl.² ........................................ C07C 43/20
[58] Field of Search ................................ 260/613 R

[56] References Cited
FOREIGN PATENTS OR APPLICATIONS
2,258,349  6/1973  Germany ............................ 260/618

*Primary Examiner*—Bernard Helfin
*Attorney, Agent, or Firm*—Gerald D. Sharkin; Richard E. Vila; Frederick H. Weinfeldt

[57] ABSTRACT

Phenoxyphenyl-butadienols, e.g., 2-(p-phenoxyphenyl)-3,4-pentadien-2-ol, and their preparation are described. The compounds are useful as anti-inflammatories.

3 Claims, No Drawings

PHENOXYPHENYL-BUTADIENOLS

This invention relates to butadienols, and more particularly, to p-phenoxyphenyl-butadienols, as well as to pharmaceutical compositions containing such compounds and to the pharmaceutical use of such compounds.

The compounds of this invention may be conveniently represented by the formula I:

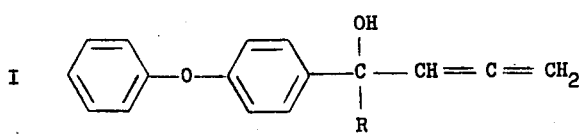

wherein
R is a hydrogen atom, methyl or ethyl, preferably methyl.

Compounds I are obtainable by reducing with a complex metal hydride, a corresponding alkynol compound of the formula II, (process a):

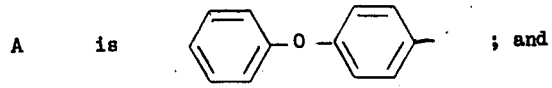

wherein
R is as defined above; and

A is 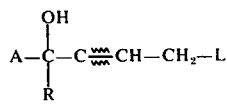 ; and

L is either
a. a quaternary ammonium radical;
b. an ether selected from the group consisting of tetrahydrofuran-2-yloxy; tetrahydropyran-2-yloxy-or 4-methoxy-tetrahydropyran-4-yloxy;
c. halo having an atomic weight of from about 19 to 127, e.g., fluoro, chloro, bromo, or iodo; or
d. a sulfonyloxy radical.

The complex hydride reducing agents may be of the formula IIIa or IIIb:

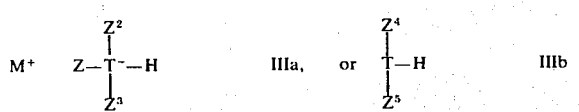

wherein
T is aluminum, gallium or boron, and
$Z^1$, $Z^2$ and $Z^3$ are, independently, a hydrogen atom, alkyl of 1 to 6 carbon atoms, alkoxy of 1 to 6 carbon atoms; or alkoxyalkoxy having from 2 to 6 total carbon atoms;
$Z^4$ and $Z^5$ are, independently, hydrogen or alkyl of 1 to 6 carbon atoms; and
M is an alkali or alkaline earth metal, such as lithium, sodium, potassium, calcium or magnesium.

Exemplary of such complex hydrides are lithium aluminum hydride, sodium dihydrobis (2-methoxyethoxy) aluminate, sodium diethyl aluminum dihydride, lithium borohydride, lithium gallium hydride, magnesium aluminum hydride, lithium diisobutylmethyl aluminum hydride, lithium trimethoxy aluminum hydride, diethyl aluminum hydride and diborane, preferably lithium aluminum hydride or sodium dihydrobis (2-methoxyethoxy) aluminate.

The complex hydrides (IIIa and IIIb) are either known and may be prepared by methods described in the literature or where not known may be prepared by methods analogous to those for preparing the known compounds. Many of the complex hydrides are commercially available.

Process (a) should be carried out in a medium which is not detrimental to the reaction, such as in an aprotic organic solvent, e.g., an ether such as diethyl ether, tetrahydrofuran or dioxane, an aromatic medium, such as benzene, toluene or pyridine or a saturated aliphatic hydrocarbon, such as pentane, hexane or octane. The medium may be a mixture or a single material. The reaction may, for example, be carried out at about $-40°$ to $+120°C$., e.g., at the boiling point of the medium. However, temperatures of from about $-10°$ to $+50°C$. are preferred. While the higher temperatures result in a faster reaction rate, reactions carried out at lower temperatures tend to give purer products. The reaction product (a Compound I) may be recovered by conventional means, e.g., by carefully adding a small amount of water or aqueous solution, e.g., aqueous ammonium chloride, or sodium hydroxide to the reaction mixture, filtering off the inorganic by-products or hydrolysis products of the hydride ion source, and then separating the Compound I product from the organic phase by such means as precipitation, extraction, crystallization, chromatography or liquid-liquid extraction. As will be appreciated by those skilled in the art, it is preferred to exclude moisture from the reaction, e.g., by use of anhydrous solvents and conditions. The reaction may be advantageously carried out in an inert atmosphere, e.g., under nitrogen gas.

The compounds of formula II in which L is a quaternary ammonium radical are compounds of formula IIa:

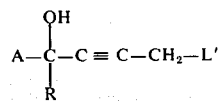

wherein
A and R are as defined above; and
L' is the radical:

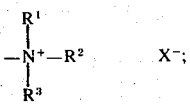

wherein $R^1$ and $R^2$ independently represent alkyl having 1 to 4 carbon atoms; unsubstituted cycloalkyl having 5 to 6 ring carbons, i.e., cyclopentyl or cyclohexyl; or together, with N, represent a heterocyclic ring having 5 to 7 members selected from the group consisting of unsubstituted pyrrolidino, piperidino, homopiperidino, morpholino, and their alkyl substituted derivatives containing from 1 to 3 alkyl groups of 1 to 4 carbon atoms;

$R^3$ represents alkyl having 1 to 4 carbon atoms, e.g., methyl, ethyl, propyl or butyl including isomeric forms where they exist, although the unbranched alkyls are preferred, especially methyl, and X is an anion derived from a mineral acid or an organic sulfonic acid, provided that X is not fluoro, e.g., iodo or methylsulfonyl.

Compounds IIa can be prepared by quaternizing a compound of the formula V:

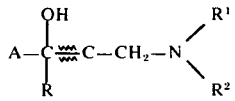     V wherein A, R, $R^1$ and $R^2$ are as defined above, with a compound of the formula VI:

$R^3X$     VI wherein $R^3$ and X are as defined above.

The quaternization can be carried out in the conventional manner, e.g., in a suitable solvent such as acetone, at a temperature of from −20° to +30°C·, neither the solvent nor the temperature being critical. A preferred compound VI is methyl iodide. The compounds of formula VI are known per se or can be prepared from known materials by conventional methods, and many are commercially available.

The compounds of formula II in which L is an ether moiety, i.e., the compounds of formula IIb:

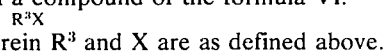     IIb wherein
A and R are as defined above, and
L″ is tetrahydrofuran-2-yloxy, tetrahydropyran-2-yloxy or 4-methoxy-tetrahydropyran-4-yloxy
can be prepared by reacting a compound of the formula VII

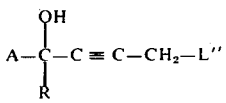     VII wherein A and R are defined above, with Grignard reagent formed by treating a compound of the formula VIII:

$HC \equiv C-CH_2-L''$     VIII wherein L″ is as defined above, with ethyl, magnesium bromide in the conventional manner for carrying out Grignard reactions.

The compounds of formulae VII and VIII used in the production of compounds IIb are known or can be prepared from known compounds using conventional techniques.

The compounds of formula II in which L is halo other than iodo, i.e., those compounds of formula IIc:

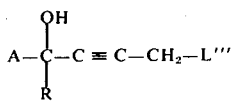     IIc wherein
A and R are as defined above, and

L‴ is fluoro, chloro or bromo can be prepared by reacting a compound of the formula IX:

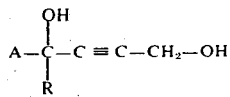     IX wherein A and R are as defined above with the appropriate halide selected from the group of thionyl chloride or bromide, phosphorus pentachloride or bromide and hydrocarbon sulfonyl fluorides, e.g., benzyl sulfonyl fluoride, tosyl fluoride and mesyl fluoride, in an organic medium such as hexane, benzene or dimethoxyglycol. For the chlorination and bromination of tertiary amine base, such as pyridine, is included in the reaction mixture and the reaction temperature is about 0° to 20°C. For the fluorination the reaction temperature is 0° to about 150°C.

Compounds of formula II in which L is iodo are conveniently prepared by reacting corresponding compounds of formula IIc in which L‴ is chloro, with sodium iodide in acetone, the reaction being carried out in conventional manner for replacing a chloro with an iodo.

The compounds of formula II in which L is a sulfonyloxy radical are compounds of formula IId:

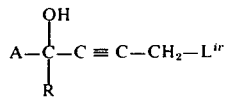     IId wherein
A and R are as defined above, and
$L^{iv}$ is a sulfonyloxy radical which may be either alkylsulfonyloxy in which the alkyl group may be substituted, e.g., halo, or unsubstituted and contain from 1 to as many as 16 or more, preferably 1 to 6 carbon atoms, e.g., methane sulfonyloxy, ethanesulfonyloxy, 3-chloropropanesulfonyloxy, or 1-hexadecanesulfonyloxy; or arylsulfonyloxy in which the aryl group is phenyl, naphthyl or substituted phenyl, which may have from 1 to 3 substituents independently selected from the group consisting of alkyl of 1 to 6 carbon atoms, alkoxy of 1 to 6 carbon atoms, halo and nitro.

Compounds IId can be prepared by reacting a compound of the formula IX above with an appropriate alkylsulfonyl chloride, such as methanesulfonyl chloride, 3-chloropropanesulfonyl chloride or 1-hexadecanesulfonyl chloride or an arylsulfonyl chloride, such as benzensulfonyl chloride, 4′-toluenesulfonyl chloride or 2-naphthalenesulfonyl chloride. This reaction is conveniently carried out in pyridine at or about room temperature.

The compounds of formula IX used in the production of compounds IIc and IId can be prepared by conventional hydrolysis of a compound of formula IIb, such as with a mineral or organic acid.

The compounds of formula V used in the preparation of Compounds IIa, above, can be prepared by reacting a compound of formula VII above with a compound of formula XI:

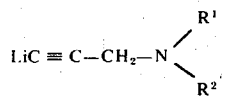     XI wherein $R^1$ and $R^2$ are as defined above. This reaction may be carried out at temperatures of 0° to 50°C., conveniently at room temperature, and in the presence of an organic solvent such as tetrahydrofuran.

The compounds of formula XI are known or can be produced in known manner by reacting a compound of the formula XIV:

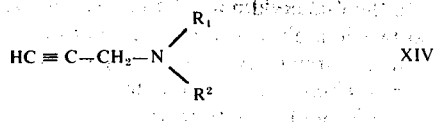

wherein $R^1$ and $R^2$ are as defined above, with lithium metal at a temperature of 0° to 50°C. in a suitable solvent such as ethylene diamine.

The compounds of formula V can also be prepared by a process (b) which involves reacting a compound of formula XII:

wherein A and R are as defined above, with a compound of formula XIII:

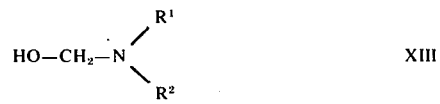

wherein $R^1$ and $R^2$ are as defined above.

In process (b), a compound of formula XII is reacted with a compound of formula XIII at a temperature of 10° to 50°C. preferably at room temperature, in the presence of an inert solvent, and in the presence of mono-valent coinage metal ion, e.g., copper ion, as catalyst, preferably cuprous chloride or cuprous oxide, although salts and the like of other coinage metals, i.e., silver and gold (I), can likewise be used. The compounds of formula XII can be prepared by reacting a compound of formula VII above in a solvent such as dimethylacetamide or dimethylsulfoxide with a suitable acetylene reagent, such as sodium or lithium acetylide conveniently at room temperature.

The compounds of formulae XIII and XIV used in the aboveidentified preparations of compounds V are known or can be produced from known materials by conventional techniques, and many are commercially available.

The compounds of formula (I) are useful because they possess pharmacological activity in animals. In particular, the compounds (I) are useful as anti-inflammatory agents as indicated by the Carrageenan induced edema test on rats (oral administration at 1 to 200 mg/kg). For such use, the compounds may be combined with a pharmaceutically acceptable carrier, and such other conventional adjuvants as may be necessary, and administered orally in such forms as tablets and capsules, elixirs, suspensions and the like or parenterally in the form of an injectable solution or suspension. The dosage administered will, of course, vary depending upon the compounds used and the mode of administration. However, in general, satisfactory results are obtained when administered at a daily dosage of from about 1 milligram to about 250 milligrams per kilogram, e.g., from about 1 milligram to about 175 milligrams per kilogram of body weight, preferably given in divided doses 2 to 4 times a day, or in sustained release form. For most mammals, the administration of from about 100 milligrams to about 3000 milligrams, e.g., from about 160 milligrams to about 2000 milligrams, of the compound per day provides satisfactory results and dosage forms suitable for internal administration comprise from about 25 milligrams to about 1500 milligrams, e.g., from about 40 milligrams to about 1000 milligrams, of the compound in admixture with a solid or liquid pharmaceutical carrier or diluent.

For the above usage, oral administration with carriers may take place in such conventional forms as tablets, dispersible powders, granules, capsules, syrups and elixirs. Such compositions may be prepared according to any method known in the art for manufacture or pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and absorption in the gastrointestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules preferably contain the active ingredient admixed with an inert diluent, e.g., calcium carbonate, calcium phosphate, kaolin, polyethylene glycol, peanut oil or sesame oil. The preferred pharmaceutical compositions from the standpoint of preparation and ease of administration are solid compositions, particularly tablets or solid or liquid diluent-filled capsules, as appropriate to the nature of the particular active ingredient.

Representative formulations for administration, 2 to 4 times a day, in treating inflammation are liquid-filled, soft gelatin capsules prepared by conventional techniques and containing the following:

| Ingredient | Weight in Milligrams |
|---|---|
| 2-(p-phenoxy-phenyl)-3,4-pentadien-2-ol | 50 |
| peanut or sesame oil | 170 |

In the following example which is illustrative of the invention, temperatures are in degrees centigrade, and room temperature is 20° to 30°C., unless indicated otherwise.

EXAMPLE 2-(p-phenoxy-phenyl)-3,4-pentadien-2-ol

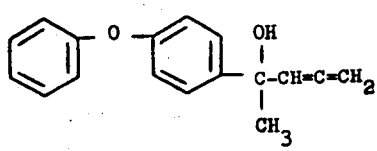

Step A: To a Grignard mixture prepared from 7.1 g. of magnesium and 32.4 g. ethyl bromide in a total of 500 ml. of dry tetrahydrofuran, 37 g. of 3-(2'-tetrahydropyranyloxy)-propyne is added dropwise. The mixture is heated for 20 minutes at reflux, cooled to room temperature and then 63 g. of 4-acetyldiphenylether dissolved in 100 ml. of dry tetrahydrofuran is added. After addition is completed, the mixture is poured onto ice, then extracted with chloroform thrice. The combined chloroform extracts are washed successively with water, 2N sodium hydroxide and brine, dried over anhydrous magnesium sulfate, filtered and evaporated to dryness to yield crude 2-(p-phenoxyphenyl)-5-(2'-tetrahydropyranyloxy)-3-pentyn-2-ol.

Step B: To 60 g. of the crude product from Step A dissolved in 400 ml. of dry tetrahydrofuran, 35 ml of a 1 molar ether solution of lithium aluminum hydride is added dropwise via syringe. After the addition is completed, the mixture is allowed to warm up to room temperature and stand for 18 hours. The mixture is then poured onto ice and extracted with methylene chloride. The methylene chloride extracts are dried over anhydrous sodium sulfate, filtered from drying agent and evaporated to dryness to yield a yellow oily crude product. The oil is refined by chromatographing on a silica gel plate using chloroform as eluent to obtain refined 2-(p-phenoxyphenyl)-3,4-pentadien-2-ol.

Repeating the procedure of this example, but replacing the 4-acetyldiphenylether used in Step (A), with an approximately equivalent amount of:

a. 1-(p-phenoxyphenyl)-propan-1-one; or
b. p-phenoxybenzaldehyde;

there is similarly obtained:

a. 3-(p-phenoxyphenyl)-4,5-hexadien-3-ol; or
b. 1-(p-phenoxyphenyl)2,3-butadien-1-ol.

What is claimed is:

1. A compound of the formula:

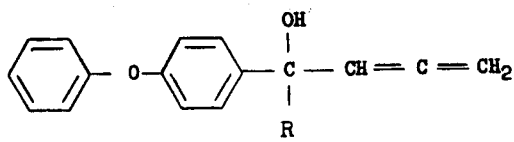

wherein R is a hydrogen atom, methyl or ethyl.

2. A compound of claim 1 in which R is a hydrogen atom or ethyl.

3. The compound of claim 2 which is 2-(p-phenoxyphenyl)-3,4-pentadien-2-ol.

* * * * *